United States Patent [19]

Mughal et al.

[11] Patent Number: 4,524,060

[45] Date of Patent: Jun. 18, 1985

[54] SLOW RELEASE PHARMACEUTICAL COMPOSITION

[75] Inventors: Ahmed S. Mughal, High Wycombe; David S. Holmes, Reading, both of England

[73] Assignee: John Wyeth & Brother Limited, Maidenhead, England

[21] Appl. No.: 546,684

[22] Filed: Oct. 28, 1983

Related U.S. Application Data

[63] Continuation-in-part of Ser. No. 375,935, May 7, 1982.

[30] Foreign Application Priority Data

May 21, 1981 [GB] United Kingdom ............ 8115678

[51] Int. Cl.³ .......................... A61K 9/28; A61K 9/52
[52] U.S. Cl. ........................................ 424/19; 424/20; 424/21; 424/22; 424/38
[58] Field of Search ...................... 424/19-22

[56] References Cited

U.S. PATENT DOCUMENTS

| | | | |
|---|---|---|---|
| 3,034,911 | 5/1962 | McKee et al. | 106/210 |
| 4,083,949 | 4/1978 | Benedikt | 424/19 |
| 4,097,606 | 6/1978 | Chavkin et al. | 424/324 |
| 4,138,475 | 2/1979 | McAinsh et al. | 424/19 |
| 4,223,008 | 9/1980 | Gregory | 424/32 |
| 4,251,518 | 2/1981 | Moore et al. | 424/180 |
| 4,304,773 | 12/1981 | Wong et al. | 424/246 |
| 4,309,404 | 1/1982 | De Neale et al. | 424/21 |

FOREIGN PATENT DOCUMENTS

| | | |
|---|---|---|
| 1467792 | 12/1968 | Fed. Rep. of Germany . |
| 46-40352 | 11/1971 | Japan . |
| 53-09315 | 1/1978 | Japan . |
| 55-122726 | 9/1980 | Japan . |
| 1218570 | 1/1971 | United Kingdom . |
| 1380171 | 1/1975 | United Kingdom . |
| 1533243 | 11/1978 | United Kingdom . |

OTHER PUBLICATIONS

Sankyo Co. Ltd., Chem. Abstr., 76, #49944u (1972) of Japan 71-40352, 29 Nov. 1971.
Kristofferson, Chem. Abstr., 87, #157116m (1977).
Asahi Chem, Chem. Abstr., 88, #141688j (1978) of Japan Kokai 78-09315, 27 Jan. 1978.
Esteve et al., Chem. Abstr., 92, #153052t (1980).
Said et al., Chem. Abstr., 94, #71361v (1981).
Asahi Chem, Chem. Abstr., 94, #52961z (1981) of Jpn. Kokai 80-122726, 20 Sep. 1980.
Wong et al., Chem. Abstr., 96, #57787y (1982) of U.S. 4,304,773.
De Neale et al., Chem. Abstr., 96, #110156v (1982) of U.S. 4,309,404.
Kornblum et al., (I) J. Pharm. Sci., 62(1): 43-49, Jan. 1973, New Tablet Disintegrating Agent: Cross-Linked Polyvinylpyrrolidone.

*Primary Examiner*—Shep K. Rose
*Attorney, Agent, or Firm*—George Tarnowski

[57] ABSTRACT

The invention provides a sustained release pharmaceutical composition comprising a mixture of micronized indoramin or a pharmaceutically acceptable salt thereof, a water-channelling agent, a wetting agent and a disintegrant, the mixture being in the form of a non-compressed pellet and having an enteric coat or a sustained release coat permeable to gastrointestinal juices. Sustained release capsules are also provided comprising a plurality of the aforementioned pellets.

12 Claims, No Drawings

SLOW RELEASE PHARMACEUTICAL COMPOSITION

This invention relates to sustained release pharmaceutical compositions containing indoramin or a pharmaceutically acceptable salt thereof and is a continuation-in-part of our co-pending application Ser. No. 375,935 filed May 7, 1982.

In U.K. Pat. No. 1,218,570 there are described and claimed a class of indole derivatives which have various pharmacological activities, especially action on the cardiovascular system. One of these compounds, indoramin, (3-[2-(4-benzamido-1-piperidyl)ethyl]indole), has demonstrated valuable antihypertensive properties in human beings. This compound is generally used in the form of its hydrochloride salt.

In the treatment of hypertensive patients where therapy continues for a considerable length of time it is desirable to employ sustained release compositions of an antihypertensive agent. This is because administration of the drug need not be as frequent as with ordinary release forms and can be reduced, for example, to once a day. As a result patient compliance with long term therapy is generally improved. Desirably sustained release forms achieve or approach steady state plasma therapeutic levels of the drug. With this aim in mind sustained release compositions are tailored to slowly, but completely release the drug in sufficient concentration into the gastrointestinal tract at a rate dependent on the dose frequency and gastrointestinal time (on average about 24 hours in the human). It is both desirable and a requirement for use in humans that a sustained release composition should be able to release at least about 80% of the drug present during transit. Formulations with less efficiency than this could have safety problems if unexpected complete release were to occur resulting in drug overdose from the 'excess' of drug present in the composition.

In attempts to prepare satisfactory sustained release formulations in pellet form containing indoramin using sustained release coatings and carriers, we have now found that dissolution of indoramin was occurring at excessively slow rates which were totally unsuitable for practical purposes.

This invention relates to pharmaceutical compositions of indoramin or a pharmaceutically acceptable salt thereof which can be used for sustained release over the gastrointestinal transit time and can provide high levels of drug release. Because the average gastric emptying time is known to be about 1 hour slow release during intestinal transit time (on average ca. 23 hours) may also be utilized in a therapeutically effective sustained release fromulation. Therefore this invention also relates to a pharmaceutical composition having sustained release properties over the intestinal transit time.

Accordingly this invention provides a sustained release pharmaceutical composition comprising a mixture of micronised indoramin or a pharmaceutically acceptable salt thereof, a water-channelling agent and a wetting agent, the mixture being in the form of a non-compressed pellet and having an enteric coat or a sustained release coat permeable to gastrointestinal juices.

By 'micronised indoramin' is meant indoramin in which the particle size has been reduced by comminution techniques employing for example fluid energy mills or roller mills, the former being preferred. It is preferred that the indoramin is micronised to a particle size in which 90% of particles are less than or equal to $15\mu$, most preferably less than or equal to $10\mu$, e.g. $5\mu$ or less.

By the term 'water-channelling agent' is meant an agent which facilitates the movement of water into the matrix of a dose form. We have found hydrophilic long chain polymers such as microcrystalline cellulose are particularly useful as exemplified by those sold under the Registered Trade Mark AVICEL.

Examples of the wetting agents useful in the composition of this invention include anionic surfactants such as sodium alkyl sulphates, sodium laurate, dioctyl sodium sulphosuccinate, sodium stearate, potassium stearate and sodium oleate; non ionic surfactants such as polyethylene glycol and polyoxyethylene esters such as those sold under the Registered Trade Mark TWEEN and cationic surfactants such as benzalkonium chloride and bis-2-hydroxyethyl oleylamine.

In a preferred dosage form, the composition of the invention is prepared by applying the ingredients, with adhesive, to an inert core which acts as a physical support, e.g. non-pareil seeds; and then providing a sustained release or enteric coating, preferably in the form of a film applied to the pellet.

In a preferred aspect this invention provides a pharmaceutical composition in capsule form comprising a plurality of sustained release pellets each containing about 50 to 95% by weight of a mixture of micronised indoramin or a pharmaceutically acceptable salt thereof, up to about 25% by weight of microcrystalline cellulose as a hydrophilic long chain polymer, up to about 10% by weight of a wetting agent and about 1 to 10% by weight of a disintegrant other than microcrystalline cellulose, the mixture being in the form of a non-compressed pellet and having an enteric coat or a sustained release coat permeable to gastro-intestinal juices, the indoramin having a particle size where 90% of the particles are less than or equal to $15\mu$, the ratio of indoramin to hydrophilic long chain polymer being about 30:1 to about 2:1 and the ratio of indoramin to wetting agent being about 300:1 to about 5:1, so as to allow at least about 80% release of indoramin into gastro-intestinal media within about 24 hours.

In the compositions of the invention the degree of micronisation and the ratios of micronised indoramin or pharmaceutically acceptable salt thereof, water-channelling agent, wetting agent and disintegrant are adjustable so that at least about 80% dissolution of drug occurs in gastrointestinal media.

The ratio of micronised indoramin or pharmaceutically acceptable salt thereof to water-channelling agent may be from about 30:1 to about 2:1, preferably about 10:1 to about 3:1. The ratio of micronised indoramin or pharmaceutically acceptable salt thereof to wetting agent may be from about 300:1 to about 5:1, preferably about 150:1 to 30:1.

The amount of indoramin or pharmaceutically acceptable salt thereof present in the mixture (i.e excluding the sustained release coat adhesive and any inert support) may comprise about 50 to 95% by weight, preferably, 75 to 90% by weight. The water channelling agent may comprise up to about 25% by weight, preferably about 4 to 20% w/w of the composition and the wetting agent up to about 10% by weight, preferably about 0.5 to 3% by weight.

The preferred compositions also comprise a disintegrant, for example, modified starch such as that sold under the Trade Mark EXPLOTAB or a crosslinked polyvinyl pyrrolidone such as sold under the Trade Mark KOLLIDON CL. Preferred range for the disintegrant is about 1 to 10% of the composition (excluding sustained release coating an any inert core), preferably 2 to 8% by weight.

Examples of sustained release coats permeable to gastro-intestinal juices are known coats such as natural waxes or mixtures of polymers especially mixtures of ethyl cellulose and a polymer selected from polyethylene glycol, hydroxypropyl cellulose, methyl cellulose, hydroxypropylmethyl cellulose and polyvinylpyrrolidone; or polyacrylate resins such as EUDRAGIT RL and RS. The coat is preferably applied as a film by depositing a solution or suspension of the coating agent on the pellet followed by evaporation of solvent carrier. However, other coat barriers are possible, e.g. enteric or sustained release coated carrier containing the pellet mixture.

Preferably the coating is a mixture of ethylcellulose (e.g. 6–50 cps) and polyethylene glycol (PEG) for example in the ratio ranging from about 9:1 to about 6:4 respectively. Preferably the molecular weight of the PEG ranges from 400 to 20,000 e.g. 2000 to 10,000. The coating may have, for example, up to about 50$\mu$ thickness depending on the release profile desired and comprise up to 15% by weight of the total composition. Examples of enteric coats are any suitable coats known in the art such as film forming substances for example hydroxypropylmethyl cellulose phthalate, polyvinyl acetate phthalate, cellulose acetate phthalate and acrylic resins. Plasticizers and lubricants may also be present. The coating may be sprayed on to the composition using a suitable solvent carrier. Typically the enteric coating comprises about 3 to about 20% w/w.

In a particularly preferred aspect this invention provides a capsule or similar unit dosage form for slow release of indoramin or a salt thereof comprising a plurality of sustained release pellets according to the aforementioned composition of this invention, if desired the pellets having varying sustained release coat thickness and quantities of indoramin, water channelling agent and/or wetting agent, and further if desired the capsule comprising a ready release quantity of indoramin or pharmaceutically acceptable salt thereof. Where an enteric coating is applied to the pellets it will obviously be desirable to incorporate the read release quantity of indoramin in the capsule to provide a rapid therapeutical effect to the user.

This invention also provides a process for preparing a sustained release pharmaceutical composition which comprises intimately mixing micronised indoramin or a pharmaceutically acceptable salt thereof, a water channelling agent and a wetting agent; forming the mixture without compression into a pellet and providing an enteric or sustained release coat permeable to gastrointestinal juices. If desired pharmaceutical excipients, e.g. fillers such as lactose may also be present in the mixture.

This invention further provides a process for preparing a sustained release capsule comprising encapsulating a plurality of pellets according to the aforementioned composition of this invention.

The following Examples describe the preparation and comparative testing of pellets according to this invention and illustrate the high levels of drug release found from our dissolution studies using an updated standard procedure designed to similate the human gastrointestinal tract.

EXAMPLE 1

Preparation of Indoramin Hydrochloride Sustained Release Pellets

A. Indoramin Uncoated Pellets

Place suitable size non pareil seeds (e.g. 840–500$\mu$) in the appropriate size of coating pan. Wet the seeds evenly by spraying on a ca. 5% adhesive solution of PVP in IPA. Apply some indoramin HCl coating powder blend to the seeds, mixing well while the pellets are rolling. Dry the pellets between coats with warm air for a few minutes. The quantities of adhesive solution and coating powder applications can proportionally be increased as the batch size increases. Continue alternate applications of adhesive solution and powder until all the coating powder blend is applied. Allow the pellets to dry. Sieve the pellets through a 1200 micron screen and over a 600 micron screen.

B. Cellulosic Coating Application

Transfer into a suitable fluidized bed stainless steel column. Spray with ethyl cellulose—PEG 4000 solution into the fluidized pellets at 40° C. Spray continuously at the approprate speed from a suitable pump and a suitable size spray nozzle. Turn on the extraction at intermittent intervals to remove vapours. Apply sufficient coating solution to increase the weight of coated pellets by the desired amount, e.g. 2–20%.

C. Using the above mentioned general procedure, pellets incorporating the composition of this invention were made by using the following ingredients:

| Coating Powder Blend | % w/w |
| --- | --- |
| Indoramin HCl micronized (90% $\leq$ 5$\mu$) | 84 |
| AVICEL pH 101 | 10 |
| EXPLOTAB | 5 |
| Sodium Lauryl Sulphate | 1 | and applying to non-pareil seeds using ca. 5% PVP in isopropyl alcohol adhesive. A 4% w/w coating of ethylcellulose—(10 cps)—PEG 4000 (8:2 w/w) sustained release coat was applied.

Final composition had 420 mg g$^{-1}$ indoramin HCl.

D. A comparative formulation not containing micronised indoramin, wetting agent or water-channelling agent was made up similarly using the following ingredients:

| Coating Powder Blend | % by weight |
| --- | --- |
| Indoramin HCl | 85% |
| EXPLOTAB | 5% |
| Talc BP | 5% |
| Kaolin Light BP | 5% | and applied to non-pareil seeds using same adhesive as in 1C and coated to 4% w/w with same sustained release coating as 1C.

Final composition had 450 mg g$^{-1}$ indoramin HCl.

EXAMPLE 2

Dissolution testing of composition from EXAMPLES 1C and 1D

The test method used was designed to model the human gastrointestinal tract. Pellets were added to dissolution medium (2 liters) which was preheated to 37°$\pm$0.5° and stirred at 50 revs/min with a 7 cm Teflon paddle situated 2.5 cm above the bottom of a 3 liter round bottomed flask.

The medium used to determine the dissolution rate was an aqueous solution of chloride ions (120 mmoles $l^{-1}$), the surface tension of which had been adjusted to $4\times10^{-2}$ $Nm^{-1}$ with Tween 80 (100 $mgl^{-1}$). The medium was initially made pH 1.5 by the presence of hydrochloric acid (0.06M) but after 1 hour the medium was changed to pH 7 by the replacement of 500 ml of the initial medium with 500 ml solution of sodium hydroxide (0.24M) and buffering salts of phosphate (ca. 0.20M) ($K_2HPO_4$ and $KH_2PO_4$). 20 ml samples of the medium were taken at selected time intervals after the introduction of the pellets and replaced by fresh medium to maintain constant volume.

Each sample was filtered through a pre-washed 1.2μ millipore filter in Swinnex holder immediately prior to assay. Samples were by uv absorbance measurement at 280 nm in 1 cm quartz cells. Comparison with standard solutions (5–30 $\mu gml^{-1}$) allowed the mg indoramin released from each sampling time to be calculated by reference to the standard graph (concentration plotted against absorbance).

The results of the variable pH dissolution test are shown in the Table below:

TABLE 1

| Formulation | pH | Percent by weight released after hours | | | | | | | |
|---|---|---|---|---|---|---|---|---|---|
| | | ½ | 1 | 1½ | 2 | 3 | 4 | 6 | 20–24 hrs |
| EXAMPLE 1C | 1.5 | 12 | 21 | | | | | | |
| (4% w/w coat) | 7 | | | 33 | 38 | 49 | 57 | * | 96 |
| EXAMPLE 1D | 1.5 | 24 | 41 | | | | | | |
| (4% w/w coat) | 7 | | | 56 | 64 | 66 | 66 | 64 | 70 |

* = not measured.

The results show that the 4% w/w coated composition of Example 1D had a relatively rapid release profile up to 2 hours followed by a virtual halt in release of indoramin for the remainder of the 24 hour time period. The similarly coated composition of Example 1C on the other hand had a more steady release profile. Additionally the composition of Example 1C produced almost complete dissolution of the indoramin in the 24 hour time period whereas that of Example 1D reached only 70% release in the same period.

EXAMPLE 3

Coated pellets on non-pareil seed cores (840–500μ) were prepared by the procedure described in Example 1 to the following formulations:

| INGREDIENT: | % Amount by weight (excluding weight of core and adhesive) Formulation: | | | | | | |
|---|---|---|---|---|---|---|---|
| | 3A | 3B | 3C | 3D | 3E | 3F | 3G |
| Indoramin HCl micronised* | 84 | 93.3 | 93.3 | 84.9 | — | 84 | 84 |
| Non micronised indoramin HCl | — | — | — | — | 84 | — | — |
| Avicel pH 101 | 10 | — | — | 10.1 | 10 | 10 | 10 |
| Explotab | 5 | 5.6 | 5.6 | 5 | 5 | — | 5 |
| Kollidon CL | — | — | — | — | — | 5 | — |
| Sodium lauryl sulphate | 1 | 1.1 | 1.1 | — | 1 | 1 | 1 |
| Potency of pellets as mg/g indoramin HCl | 410 | 527 | 547 | 547 | 487 | 448 | 425 |
| Seed size (μ) | 840–700 | 595–500 | 840–700 | 700–595 | 595–500 | 595–500 | 840–700 |

*Degree of micronisation 90% of particles ≤ 5μ

Pellets 3A, 3B, 3C, 3D and 3E were given a sustained release coat, the coating solution containing 8% w/v ethyl cellulose and 2% w/v polyethylene glycol 4000. Pellets 3F and 3G were given an enteric coat, the coating solution containing 8% w/v hydroxypropylmethyl cellulose phthalate and 5% w/v glycerol triacetate. The pellets had the following coating weights:

| Pellet: | 3A | 3B | 3C | 3D | 3E | 3F | 3G |
|---|---|---|---|---|---|---|---|
| Coating weight: (% w/w relative to uncoated pellet) | 4 | 3.2 | 3.3 | 3.6 | 4 | 10.3 | 10 |

EXAMPLE 4

Dissolution studies were carried out on the pellets 3A–3G above according to the procedure described in Example 2, but modified slightly in the following manner:

(i) Surface tension was controlled using Tween 20 (100 $mgl^{-1}$).

(ii) The change in pH was modified so that the final pH was 6.8±0.05 (not 7.0). This was achieved by the replacement of 1 liter of initial medium after 1 hour with 1 liter of a solution, at 37° C., of sodium hydroxide (0.12M) and buffering salts of phosphate (ca. 0.1M) ($K_2HPO_4$ and $KH_2PO_4$).

(iii) A further 1 liter of medium was replaced at 6 hours with 1 liter of solution, at 37° C., of buffering salts of phosphate (0.05M) ($K_2HPO_4$ and $KH_2PO_4$) having a pH of 6.8.

The results of the variable pH dissolution test are tabulated below (TABLE 2) and some are also illustrated in the accompanying FIG. 1.

TABLE 2

| Formulation | pH | % (w/w) released after hours: | | | | | | | | | | |
|---|---|---|---|---|---|---|---|---|---|---|---|---|
| | | ½ | 1 | 1½ | 2 | 3 | 4 | 6 | 7 | 8 | 10 | 24 |
| 3A | 1.5 | 13 | 26 | | | | | | | | | |
| | 6.8 | | | 40 | 46 | * | 62 | 70 | * | * | * | 94 |
| 3B | 1.5 | 7 | 14 | | | | | | | | | |
| | 6.8 | | | 30 | 35 | 44 | 48 | 53 | * | 53 | * | * |
| 3C | 1.5 | 8 | 15 | | | | | | | | | |
| | 6.8 | | | 30 | 39 | 45 | 48 | 52 | * | 52 | * | * |
| 3D | 1.5 | 21 | 32 | | | | | | | | | |
| | 6.8 | | | 43 | 46 | 50 | 52 | 55 | * | 56 | * | * |
| 3E | 1.5 | 4 | 9 | | | | | | | | | |
| | 6.8 | | | 24 | 33 | 40 | 44 | 49 | * | 51 | * | * |
| 3F | 1.5 | 2 | 3 | | | | | | | | | |
| | 6.8 | | | 13 | 15 | 19 | 21 | 27 | 31 | * | 42 | 91 |
| 3G | 1.5 | <1 | 2 | | | | | | | | | |
| | 6.8 | | | 21 | 33 | 44 | 52 | 62 | 75 | * | * | 87 |

* = not measured.

Formulations 3A, 3F and 3G are all composition of the present invention and the dissolution results show that 3A, 3F and 3G achieve almost complete release of indoramin hydrochloride in the 24 hour time period.

Formulations 3B, 3C, 3D and 3E on the other hand virtually halted release of indoramin HCl after 3 hours. The difference in behaviour is more readily apparent from the accompanying FIG. 1 where the dissolution rates of formulations 3B, 3C, 3D and 3E are compared graphically with formulation 3A. Formulation 3A can be seen to be markedly superior from its ability to reach almost total release of indoramin HCl at the 24 hour time point.

By studying Table 2 and the formulations given in Example 3 it can be seen that the micronised indoramin, water channelling agent and wetting agent are essential ingredients if the desired, almost complete, dissolution is to occur over the 24 hour time period. Compare for example: 3A and 3B which show water channelling agent is essential: 3A and 3E which show micronisation is essential; and 3A and 3D which show wetting agent is essential.

Furthermore 3A and 3G show that either sustained release or enteric coats may be employed.

EXAMPLE 5

Pellets according to the invention, on non-pareil seed cores, and prepared by the procedure described in Example 1 and have the following formulations prior to coating with ethyl cellulose/PEG 4000 slow release coat:

| Ingredient | % amount by weight* | | | | | |
|---|---|---|---|---|---|---|
| | H | I | J | K | L | M |
| Indoramin HCl (micronised, 90% ≦ 5μ) | 84 | 80 | 85 | 86 | 85 | 80 |
| Avicel pH 101 | 10 | 15 | 9 | 5 | 9 | 15 |
| Explotab | 5 | 4 | 4 | 8 | 4 | 2 |
| Sodium lauryl sulphate | | 1 | 2 | 1 | | 3 |
| Dioctyl sodium sulphosuccinate | 1 | | | | 2 | |

*Excluding weight of core and adhesive.

We claim:

1. A pharmaceutical composition in capsule form comprising a plurality of sustained release pellets each containing about 50 to 90% by weight of a mixture of micronised indoramin or a pharmaceutically acceptable salt thereof, about 4 to 25% by weight of microcrystalline cellulose as a hydrophilic long chain polymer, about 0.5 to 10% by weight of a wetting agent and about 1 to 10% by weight of a disintegrant other than microcrystalline cellulose, the mixture being in the form of a non-compressed pellet and having an enteric coat or a sustained release coat permeable to gastro-intestinal juices, the indoramin having a particle size where 90% of the particles are less than or equal to 15μ, the ratio of indoramin to hydrophilic long chain polymer being about 30:1 to about 2:1 and the ratio of indoramin to wetting agent being about 300:1 to about 5:1 so as to allow at least about 80% release of indoramin into gastro-intestinal media within about 24 hours.

2. A composition as claimed in claim 1 in which the ratio of micronised indoramin or pharmaceutically acceptable salt thereof to hydrophilic long chain polymer is from about 10:1 to about 3:1.

3. A composition as claimed in claim 1 in which the ratio of micronised indoramin or pharmaceutially acceptable salt thereof to wetting agent is from about 150:1 to 30:1.

4. A composition as claimed in claim 1 wherein 90% of the particles are 5μ or less.

5. A composition as claimed in claim 1 in which the indoramin or pharmaceutically acceptable salt thereof comprises about 75 to about 90% by weight of the mixture.

6. A composition as claimed in claim 1 in which the wetting agent comprises from about 0.5 to 3% by weight of the mixture.

7. A compound as claimed in claim 1 in which the microcrystalline cellulose comprises about 4 to 20% by weight of the mixture.

8. A composition as claimed in claim 1 in which the wetting agent is a sodium alkyl sulphate, sodium laurate, dioctyl sodium sulphosuccinate, sodium stearate, potassium stearate, sodium oleate, polyethylene glycol, a polyoxyethylene ester, benzalkonium chloride or bis-2-hydroxyethyl oleylamine.

9. A composition as claimed in claim 1 in which the pellet is prepared by applying the mixture in layers, bound by adhesive, to an inert core.

10. A composition as claimed in claim 9 in which the inert core is a non-pareil seed of from about 500 to 840μ diameter.

11. A sustained release pharmaceutical composition in accordance with claim 1 comprising a capsule containing a plurality of pellets, each pellet formed by applying an intimate mixture comprising abouut 50 to 90% by weight of micronised indoramin hydrochloride in which 90% of the particles have a particle size ≦5μ, about 4 to 25% by weight of microcrystalline cellulose, about 1 to 10% by weight of a disintegrant other than microcrystalline cellulose and about 0.5 to 10% by weight of a wetting agent in layers bound by adhesive to an inert core; said pellet having a sustained release or enteric coat applied as a film, the ratios of indoramin hydrochloride to microcrystalline cellulose and wetting agent being in the range from about 10:1 to about 3:1 and about 150:1 to about 30:1, respectively.

12. A composition as claimed in claim 1 in which the disintegrant is about 2 to 8% by weight of the mixture.

* * * * *